United States Patent [19]

Jean, Jr. et al.

[11] Patent Number: 4,616,367

[45] Date of Patent: Oct. 14, 1986

[54] HEADBAND WITH DETACHABLE LENSES

[76] Inventors: Joseph A. Jean, Jr., 1631 E. Grove Pl., Fullerton, Calif. 92631; Lynne Laurence, 1020 Riverside Dr., #46, Burbank, Calif. 91506

[21] Appl. No.: 671,479

[22] Filed: Nov. 14, 1984

[51] Int. Cl.4 .................................................. A61F 9/02
[52] U.S. Cl. .......................................... 2/452; 2/453; 2/DIG. 11; 351/155
[58] Field of Search ...................... 2/453, 452, 426, 10, 2/199, DIG. 11, 171; 351/110, .155, 156

[56] References Cited

U.S. PATENT DOCUMENTS

| 1,502,820 | 7/1924 | Funk | 2/453 |
|---|---|---|---|
| 1,517,009 | 11/1924 | Kniffen | 351/59 |
| 1,660,896 | 2/1928 | Tallman et al. | 2/10 |
| 2,271,703 | 2/1942 | McNeill | 2/453 |
| 4,152,051 | 5/1979 | Van Tiem | 351/155 X |
| 4,393,519 | 7/1983 | Nicastro | 2/DIG. 11 |

FOREIGN PATENT DOCUMENTS 0196554  8/1957  Austria ..................................... 2/453

Primary Examiner—Peter Kerbon

[57] ABSTRACT

A headband with detachable lenses wherein the lenses are movable laterally to accommodate an individual's inter-pupillary distance and also angularly to accommodate the individual's forehead angle.

6 Claims, 6 Drawing Figures

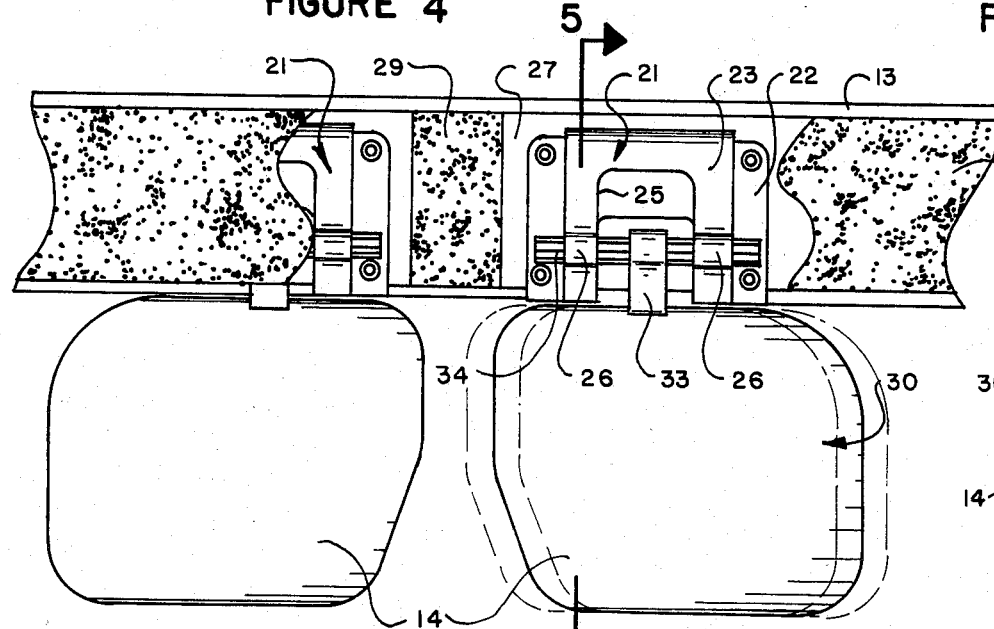
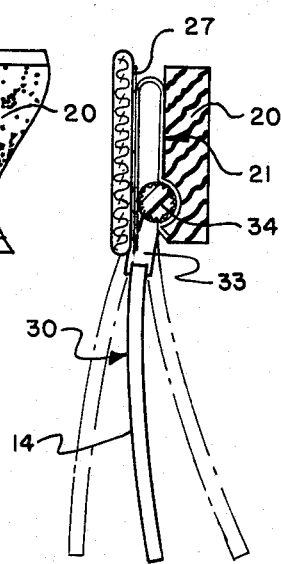
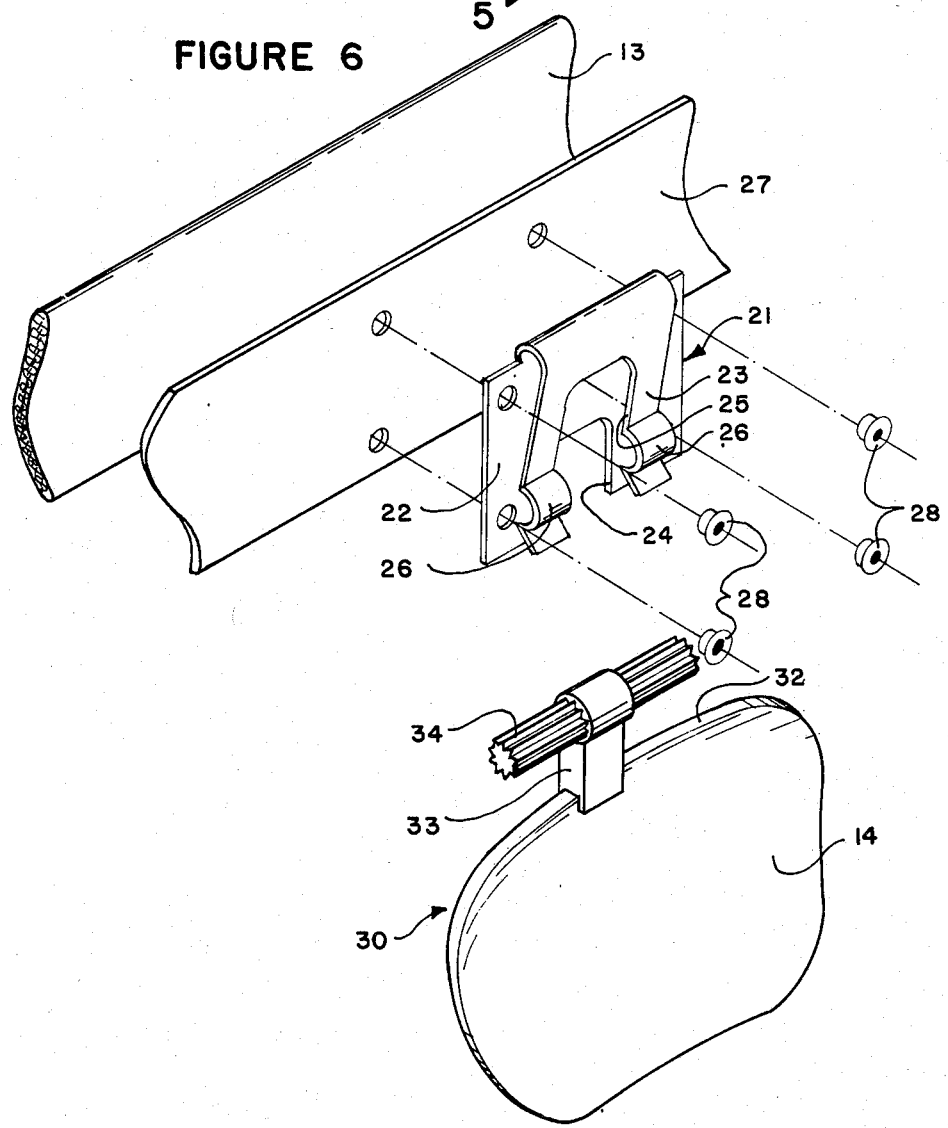

HEADBAND WITH DETACHABLE LENSES

BACKGROUND OF THE INVENTION

1. Field of the Invention

The present invention relates to a headband with detachable lenses and, more particularly, to a headband which is adapted to removably receive a pair of lenses which are adjustable both laterally and angularly.

2. Description of the Prior Art

It is well known that many individuals wear eyeglasses, both prescription glasses and glasses which function primarily or solely as sunglasses. A conventional pair of glasses rests on the bridge of the nose and includes temple pieces which rest on the ears. Under most circumstances, this does not present any particular problem.

On the other hand, where there is a lot of physical activity, such as in skiing, playing tennis, jogging or the like, people generally experience difficulty when wearing conventional glasses. Glasses have a tendency to flop up and down and/or bounce on the wearer's nose such that the glasses are either a nuisance or need constant readjustment. The usual solution to this problem is to attempt to retain the glasses in place by the use of an elastic cord which is attached to the ends of the temple pieces of the glasses and extends behind the back of the head of the wearer. Even when effective in holding the glasses in place, the elastic cord tends to accentuate rather than eliminate the pressure of the glasses on the bridge of the nose.

Strenuous physical activity is not the only circumstance where conventional glasses are objectionable. Many individuals who do not wear glasses regularly, but merely occasionally wear sunglasses, find it annoying to experience a pair of glasses resting on their nose and ears. Also, many individuals find conventional glasses and their temple pieces unattractive.

In response to these objections to conventional glasses, it has been proposed to incorporate, within a headband, a means for receiving individual lenses which function as a pair of glasses or sunglasses, while eliminating the need for eyeglass frames which rest on the nose and on the ears. However, none of the devices proposed heretofore have been entirely satisfactory. In most cases, the finished product has not been very attractive, limiting its use to a small percentage of those who would otherwise benefit from such a product. In other cases, the lenses have not been removable. Removable lenses are highly desirable so that the headband can be washable without risking damage to the lenses.

With some devices, it has been recognized that it is necessary for the individual lenses to be adjustable laterally to accommodate the user's inter-pupillary distance. However, it is generally not been recognized that it is also necessary for the lenses to be adjustable angularly to accommodate various angles of user foreheads. Without this angular adjustment, the lenses may either project outwardly, being cosmetically unattractive, or project inwardly and contact the face of the wearer.

SUMMARY OF THE INVENTION

According to the present invention, there is provided a headband with detachable lenses which overcomes the objections experienced with products of this nature developed heretofore. The present article is both attractive and functional, suitable for a wide variety of uses. The lenses are readily removable, but once placed within the headband, are securely held in a desired position. The present article completely eliminates the need for eyeglass frames which rest on the nose and on the ears. Instead, lenses are attached to a headband in such a way that they are movable laterally to accommodate the user's inter-pupillary distance and angularly to accommodate various angles of foreheads.

Briefly, the present headband with detachable lenses comprises a headband adapted to encircle the head of a user; a strip of moisture-absorbing material secured to one side of the headband; a pair of generally U-shaped spring clips positioned in parallel, spaced relationship and retained between the headband and the moisture-absorbing material strip, with the open end of the clips extending transverse to the longitudinal dimension of the headband; and a pair of lenses, each lens including an elongate cylindrical member extending parallel to the top edge thereof and a projection for interconnecting the lens and the cylindrical member, the spring clips being adapted to independently receive the members of the lenses, the lenses being adjustable relative to the clips, both laterally and angularly about the axes of the cylindrical members.

OBJECTS, FEATURES AND ADVANTAGES

It is therefore the object of the present invention to solve the problems encountered heretofore in developing a headband with detachable lenses. It is a feature of the present invention to solve these problems by the provision of a novel pair of spring clips adapted to receive a pair of members attached to the lenses whereby the lenses are detachable and fully adjustable. An advantage to be derived is an attractive article. Another advantage is a highly functional article, one which is susceptible to a wide variety of uses. Still another advantage is a headband with detachable lenses. Another advantage is a headband with detachable lenses which are adjustable laterally and angularly. Another advantage is a headband with detachable lenses which is foldable to a position small enough to permit the entire assembly to be placed in a shirt pocket.

Still other objects, features and attendant advantages of the present invention will become apparent to those skilled in the art from a reading of the following detailed description of the preferred embodiment constructed in accordance therewith, taken in conjunction with the accompanying drawings wherein like numerals designate like parts in the several figures and wherein:

BRIEF DESCRIPTION OF THE DRAWINGS

FIG. 4 is an enlarged, partial, rear elevation view with a portion of the foam strip removed, showing the details of the spring clip;

FIG. 5 is a sectional view taken along the line 5—5 in FIG. 4; and

FIG. 6 is an exploded perspective view showing the relationship between the headband, the strip of interfacing material, one of the spring clips and one of the removable lenses.

DESCRIPTION OF THE PREFERRED EMBODIMENT

Figure 1:
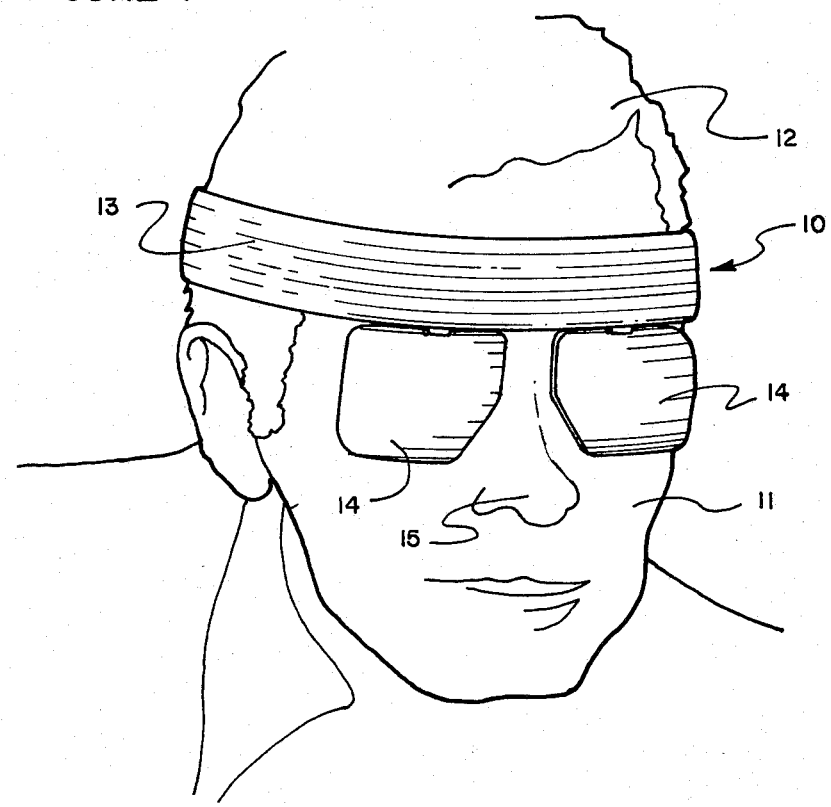
FIG. 1 is an illustration showing the present headband with detachable lenses in place on the face and around the head of the user.
Figure 2:
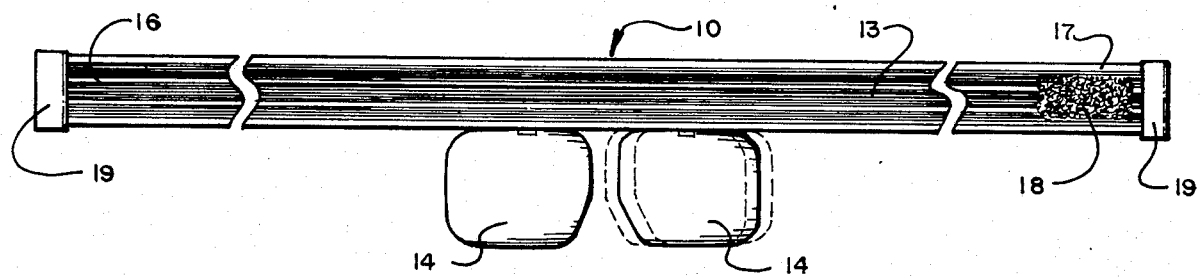
FIG. 2 is a front elevation view of the present headband with detachable lenses.

Referring now to the drawings, and, more particularly, to FIG. 1 thereof, there is shown the present article, generally designated 10, in place on the face 11 and around the head 12 of a wearer. It should be immediately noted that article 10 includes a headband 13 and a pair of detachable lenses 14. Lenses 14 are fully supported by headband 13 so that they do not rest on the wearer's nose 15. Article 10 is attractive and functional, susceptible to a wide variety of uses.

The details of article 10 will appear from an examination of FIGS. 2-6 in conjunction with the following description. Headband 13 is an elongate strip which is adapted to extend entirely around head 12. Headband 13 will generally consist of a material with some elasticity. While headband 13 can be made in one continuous piece, it preferably includes first and second ends 16 and 17 which are provided with suitable fastening means, such as complementary strips of Velcro 18. Ends 16 and 17 of headband 13 are preferably finished with molded plastic or other material end caps 19 which prevent the material of headband 13 from unraveling and also to provide a finished look.

Article 10 also includes a relatively thick strip 20 of a highly moisture-absorbing material which is secured to one side of headband 13. Strip 20 performs a number of functions, but primarily serves to absorb moisture from face 11 during strenuous physical activity. As will be more apparent hereinafter, strip 20 also adapts article 10 to face 11.

A pair of identical, generally U-shaped spring clips 21 are positioned in parallel, spaced relationship between headband 13 and moisture-absorbing material strip 20. As shown in FIG. 5, the spring clips 21 have a generally U-shape when viewed from the side. In addition, as seen in FIGS. 4 and 6, both the front 22 and rear 23 surfaces of spring clips 21 also have a generally U-shape to provide central slots 24 and 25, respectively. The reason for this will appear more fully hereinafter. At this time, it should be noted that front surface 22 of each spring clip 21 is generally planar and that rear surface 23 includes a pair of coaxial, semi-cylindrical sections 26.

Figure 3:
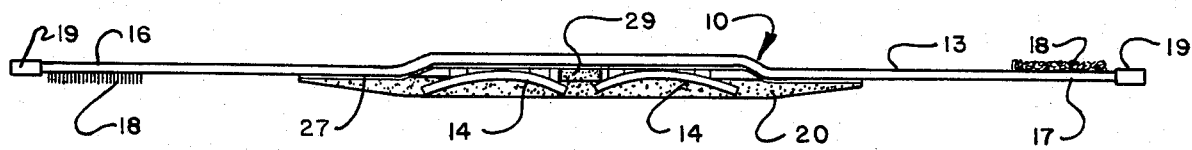
FIG. 3 is a bottom plan view thereof.

In order to secure spring clips 21 between headband 13 and strip 20, article 10 includes a strip of interfacing material 27 which has a length approximately the same as the length of strip 20. Clips 21 are securely fastened to strip 27, such as by means of a plurality of rivets 28, as shown in FIGS. 4 and 6. Once clips are secured to strip 27, strip 27 can be bonded to headband 13, as shown in FIGS. 3 and 5. Strip 20 is then bonded to strip 27, also as shown in FIGS. 3 and 5, strip 20 absorbing sections 26 in surface 23 of clips 21. To fill up the space between strips 20 and 27, between clips 21, a small strip of foam 29 may be used. It should also be noted that in the normal resting position of clips 21, there is a spring force so that surfaces 22 and 23 are in contact, below sections 26.

Finally, article 10 includes a pair of identical lens members 30, each of which includes a lens 14, which may be a prescription lens or a sun lens or both. Extending transversely from the upper edge of each lens 14 is a support member 33 which serves to support an elongate, generally cylindrical member 34, member 34 extending parallel to upper edge 32 of lens 14. The diameter of cylindrical member 34 is approximately the same as the diameter of sections 26. In the preferred embodiment, cylindrical member 34 includes serrations which extend along the length thereof.

The operation of article 10 should be apparent from the above description and the drawings. Headband 13, strips 20, 27 and 29 and the pair of spring clips 21 are assembled into a unitary structure. Such structure can be readily placed in a washing machine or otherwise cleaned to refresh strip 20 which will normally perform a perspiration-absorbing function in use. For this reason, the material of spring clips 21 will be selected so as to be noncorrosive. It should also be noted that by using two spring clips 21, headband 13 is foldable so that even with lens members 30 attached thereto, article 10 can be reduced to a size which is small enough to place in the shirt pocket of a user.

Lens member 30, including lens 14 and members 33 and 34, may be manufactured in any suitable manner. According to the preferred embodiment of the invention, lens members 30 are preferrably molded in one piece. When it is desired to attach lens members 30 to headband 13, cylindrical members 34 are simply placed between surfaces 22 and 23 of spring clips 21. The lowest ends of surfaces 23 of spring clips 21 are spread outwardly to facilitate the insertion of cylindrical members 34 between surfaces 22 and 23. In any event, lens members 30 are moved laterally until cylindrical members 34 snap into sections 26. The force of spring clips 21 is adjusted so as to resist the lateral movement and rotation of cylindrical members 34 under all normal circumstances.

As will be apparent from an inspection of FIGS. 4 and 5, the dimensions of spring clips 21 and lens members 30 are selected such that lens members 30 are movable laterally relative to spring clips 21, the amount of movement being selected so that article 10 will accommodate the usual inter-pupillary distance variations found with different individuals. In addition, support members 33 extend within slots 24 and 25 in surfaces 22 and 23, respectively, in spring clips 21. Thus, lens members 30 may be rotated about the axes of cylindrical members 34, as shown in FIG. 5, to accommodate various angles of foreheads. With the presently contemplated embodiment, it is envisioned that lens members 30 may be moved angularly through an angle of 10° on either side of the vertical.

While the invention has been described with respect to the preferred physical embodiment constructed in accordance therewith, it will be apparent to those skilled in the art that various modifications and improvements may be made without departing from the scope and spirit of the invention. Accordingly, it is to be understood that the invention is not to be limited by the specific illustrative embodiment, but only by the scope of the appended claims.

We claim:

1. An article comprising, in combination:
   a headband adapted to encircle the head of a user;
   a strip of moisture-absorbing material secured to one side of said headband;
   a pair of clips positioned in parallel, spaced relationship and retained between said headband and said moisture-absorbing material strip, with the open ends of said clips extending transverse to the longitudinal dimension of said headband; and
   a pair of lenses, each of said lenses including an elongate member extending parallel to the top edge thereof and means for interconnecting each of said lenses and the corresponding one of said members, said clips being adapted to independently receive said members of said lenses, said lenses being adjustable relative to said clips both laterally and angularly about the axes of said elongate members.

2. The article of claim 1, wherein said lenses are removable from said clips and said headband.

3. The article of claim 1, wherein each said elongate member is generally cylindrical and includes serrations therein whereby said clips retain said lenses positively in position when placed there by said user.

4. The article of claim 1, further comprising:
a strip of interfacing material positioned and retained between said headband and said moisture-absorbing material strip, said spring clips being fastened to said interfacing material strip.

5. The article of claim 4, wherein portions of said headband, said moisture-absorbing material strip, and said interfacing material strip are bonded together.

6. The article of claim 1, wherein each of said spring clips includes a front and a rear surface, each of said surfaces being generally U-shaped to provide a pair of slots, said interconnecting means extending within said slots and permitting angular adjustment of said lenses relative to said clips.

* * * * *